US012357491B2

(12) United States Patent
Sharpe (10) Patent No.: US 12,357,491 B2
(45) Date of Patent: Jul. 15, 2025

(54) APPARATUS FOR KNEE EXTENSION FOR USE WITH KNEE BRACE

(71) Applicant: Jeffrey Lawrence Sharpe, Park City, UT (US)

(72) Inventor: Jeffrey Lawrence Sharpe, Park City, UT (US)

( * ) Notice: Subject to any disclaimer, the term of this patent is extended or adjusted under 35 U.S.C. 154(b) by 200 days.

(21) Appl. No.: 18/471,827

(22) Filed: Sep. 21, 2023

(65) Prior Publication Data

US 2025/0099282 A1 Mar. 27, 2025

(51) Int. Cl.
*A61F 5/042* (2006.01)
*A61F 5/01* (2006.01)

(52) U.S. Cl.
CPC ............ *A61F 5/042* (2013.01); *A61F 5/0125* (2013.01)

(58) Field of Classification Search
CPC ...... A61F 5/042; A61F 5/0125; A61F 5/0123; A61F 5/04; A61F 5/0102; A61F 5/01; A61F 5/00; A61F 5/0151; A61F 5/0153; A61F 5/0106
See application file for complete search history.

(56) References Cited

U.S. PATENT DOCUMENTS 5,236,333 A * 8/1993 Barba, Jr. ............... A61H 1/024
602/5
7,309,305 B2 * 12/2007 Nichols ............ A63B 21/00047
482/148

FOREIGN PATENT DOCUMENTS

DE 102020126952 A1 * 6/2021 ............... A41D 1/06

* cited by examiner

*Primary Examiner* — Tarla R Patel
(74) *Attorney, Agent, or Firm* — STETINA GARRED BRUCKER & NEWBOLES (57) ABSTRACT

An apparatus for knee extension for use with a knee brace. The apparatus includes a frame having first and second frame sides, a foot support end and a handle end. The apparatus includes a heel support and a thigh support each spanning across the frame sides. The apparatus includes an upper exterior attachment member attached to the first frame side and further attachable to an upper exterior bar element of the knee brace with the knee brace being worn by the user. The apparatus includes a lower exterior attachment member attached to the first frame side and further attachable to a lower exterior bar element of the knee brace with the knee brace being worn by the user.

19 Claims, 6 Drawing Sheets

APPARATUS FOR KNEE EXTENSION FOR USE WITH KNEE BRACE

CROSS-REFERENCE TO RELATED APPLICATIONS

Not Applicable

STATEMENT RE: FEDERALLY SPONSORED RESEARCH/DEVELOPMENT

Not Applicable

BACKGROUND

Knee braces worn about a leg of a user are often used in conjunction with knee injury or knee surgery recovery processes. A typical knee brace includes structural supports in the form of an upper exterior bar element, a lower exterior bar element, and an exterior hinge disposed between the upper exterior bar element and the lower exterior bar element. The knee brace includes a fabric or other flexible material that encompasses these structural supports and is used to secure the knee brace to the leg of the user. During the recovery process it may be desirable to maintain the upper leg and the lower leg to be held or maintained at a particular angle with respect to each other. This angle may be prescribed or desired to be at a specific angular orientation between the upper leg and the lower leg during different phases of the knee recovery process. Some knee braces allow for the hinge to be locked at specific desired angles. Generally speaking, it is often a goal to allow the lower leg to be able to move forward-most as possible towards an orientation of the lower leg approaching parallel to the upper leg for full knee extension. This facilitates the ligaments, muscles and other structures associated with the knee to properly heal and achieve desired mobility. However, performing such knee extensions while the knee is still in the recovery process may pose risks of further injury of recovery setbacks if not done correctly with the proper alignment or too much extension.

In view of the foregoing, there is a need in the art for an improved apparatus for knee extension activities.

BRIEF SUMMARY

According to an aspect of the invention, there is provided a knee extension apparatus for knee extension for use with a knee brace worn about a leg of a user. The knee brace has an upper exterior bar element, a lower exterior bar element, and an exterior hinge disposed between the upper exterior bar element and the lower exterior bar element. The upper exterior bar element is positioned along an upper leg of the user with the knee brace worn by the user. The lower exterior bar element is positioned along a lower leg of the user with the knee brace worn by the user. The exterior hinge is positioned at the knee of the user with the knee brace worn by the user. The apparatus includes a frame defining a generally elongated rectangular-like frame having a generally parallel first and second frame sides, a foot support end and a handle end. The foot support end is bent toward the handle end. The apparatus further includes a heel support. The heel support is disposed adjacent the foot support end and spanning across the first and second frame sides. The heel support is sized and configured to engage a heel of the user with a bottom of a foot of the user being disposed against the foot support end. The apparatus further includes a thigh support spanning across the first and second frame sides. The thigh support is sized and configured to engage a thigh of the user with the foot of the user being disposed against the foot support end. The apparatus further includes an upper exterior attachment member attached to the first frame side and further attachable to the upper exterior bar element of the knee brace with the knee brace being worn by the user and the heel support disposed against the lower leg adjacent the heel of the user and the thigh support disposed against the thigh of the user. The apparatus further includes a lower exterior attachment member attached to the first frame side and further attachable to the lower exterior bar element of the knee brace with the knee brace being worn by the user and the heel support disposed against the lower leg adjacent the heel of the user and the thigh support disposed against the thigh of the user.

According to various embodiments, the upper exterior attachment member may include an upper exterior frame end attached to the first frame side and an upper exterior brace end attachable to the upper exterior bar element. The upper exterior attachment member may be attachable to the upper exterior bar element of the knee brace with the knee brace being worn by the user and the heel support disposed against the lower leg adjacent the heel of the user and the thigh support disposed against the thigh of the user with a distance between the upper exterior frame end and the upper exterior brace end being adjustable. The lower exterior attachment member may be attachable to the lower exterior bar element of the knee brace with the knee brace being worn by the user and the heel support disposed against the lower leg adjacent the heel of the user and the thigh support disposed against the thigh of the user with a distance between the lower exterior frame end and the lower exterior brace end being adjustable. The upper exterior attachment member may include an upper exterior frame end, and an upper exterior brace end. The upper exterior frame end may be attached to the first frame side and the upper exterior brace end is attachable to the upper exterior bar element of the knee brace with the knee brace being worn by the user and the heel support disposed against the lower leg adjacent the heel of the user and the thigh support disposed against the thigh of the user. The upper exterior frame end may be repositionable along the first frame side in fixed attachment.

Further, the lower exterior attachment member may include a lower exterior frame end, and a lower exterior brace end. The lower exterior frame end may be attached to the first frame side and the lower exterior brace end is attachable to the upper exterior bar element of the knee brace with the knee brace being worn by the user and the heel support disposed against the lower leg adjacent the heel of the user and the thigh support disposed against the thigh of the user. The lower exterior frame end may be repositionable along the first frame side in fixed attachment.

In addition, the knee brace may further have an upper interior bar element generally parallel to the upper exterior bar element, a lower interior bar element generally parallel to the lower exterior bar element, and an interior hinge disposed between the upper interior bar element and the lower interior bar element. The upper interior bar element is positioned along the upper leg of the user with the knee brace worn by the user. The lower interior bar element is positioned along the lower leg of the user with the knee brace worn by the user. The interior hinge is positioned with the knee between the interior hinge and the exterior hinge with the knee brace worn by the user. The apparatus may further include an upper interior attachment member attached to the second frame side and further attachable to the upper interior bar element of the knee brace with the knee brace being worn by the user and the heel support disposed against the lower leg adjacent the heel of the user and the thigh support disposed against the thigh of the user. The apparatus may further include a lower interior attachment member attached to the second frame side and further attachable to the lower interior bar element of the knee brace with the knee brace being worn by the user and the heel support disposed against the lower leg adjacent the heel of the user and the thigh support disposed against the thigh of the user. The first frame side may be attachable to the upper exterior bar element of the knee brace at a variable angle with the knee brace being worn by the user and the heel support disposed against the lower leg adjacent the heel of the user and the thigh support disposed against the thigh of the user.

According to another aspect of the invention, there is provided a method for knee extension for use with a knee brace worn about a leg of a user. The knee brace has an upper exterior bar element, a lower exterior bar element, and an exterior hinge disposed between the upper exterior bar element and the lower exterior bar element. The method includes wearing the knee brace by the user with the upper exterior bar element being positioned along an upper leg of the user, with the lower exterior bar element being positioned along a lower leg of the user, and with the exterior hinge being positioned at the knee of the user. The method further includes providing an apparatus including a frame defining a generally elongated rectangular-like frame having a generally parallel first and second frame sides, a foot support end and a handle end, the foot support end being bent toward the handle end. The apparatus further includes a heel support. The heel support is disposed adjacent the foot support end and spanning across the first and second frame sides. The heel support is sized and configured to engage a heel of the user with a bottom of a foot of the user being disposed against the foot support end. The apparatus further includes a thigh support spanning across the first and second frame sides. The thigh support is sized and configured to engage a thigh of the user with the foot of the user being disposed against the foot support end. The method further includes positioning the apparatus on the user with the leg of the user extending generally along and between the first and second frame sides with a heel of the leg of the user supported by the heal support and the thigh support disposed against the thigh of the user. The method further includes attaching the first frame side to the upper exterior bar element. The method further includes attaching the first frame side to the lower exterior bar element. The method further includes pulling the handle end towards a torso of the user.

According to various embodiments, the step of attaching the first frame side to the upper exterior bar element may include providing an upper exterior attachment member attached to the first frame side and the upper exterior bar element. The step of attaching the first frame side to the upper exterior bar element may further include repositioning the upper exterior attachment member along the first frame side in fixed attachment. The step of attaching the first frame side to the upper exterior bar element may further include adjusting a length of the upper exterior attachment member. The step of attaching the first frame side to the lower exterior bar element may include providing a lower exterior attachment member attached to the first frame side and the lower exterior bar element. The step of attaching the first frame side to the lower exterior bar element may further include repositioning the lower exterior attachment member along the first frame side in fixed attachment. The step of attaching the first frame side to the lower exterior bar element may further include adjusting a length of the lower exterior attachment member.

Further, the knee brace may further have an upper interior bar element generally parallel to the upper exterior bar element, a lower interior bar element generally parallel to the lower exterior bar element, and an interior hinge disposed between the upper interior bar element and the lower interior bar element. The upper interior bar element may be positioned along the upper leg of the user with the upper leg between the upper exterior bar element and the upper interior bar element with the knee brace worn by the user. The lower interior bar element may positioned along the lower leg of the user with the lower leg between the lower exterior bar element and the lower interior bar element with the knee brace worn by the user. The interior hinge may positioned with the knee between the exterior hinge and the interior hinge with the knee brace worn by the user. The step of wearing the knee brace may further include wearing the knee brace by the user with the upper leg between upper interior bar element and the upper exterior bar element, the lower leg between the lower exterior bar element and the lower interior bar element, and the knee between the exterior hinge and the interior hinge. The method may further include attaching the second frame side to the upper interior bar element and attaching the second frame side to the lower interior bar element.

According to another aspect of the invention, there is provided an integrated knee extension system for knee extension. The system includes the knee brace and the knee extension apparatus as contemplated above.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments. It is further understood that the use of relational terms such as top and bottom, first and second, and the like are used solely to distinguish one entity from another without necessarily requiring or implying any actual such relationship or order between such entities.

Figure 1:
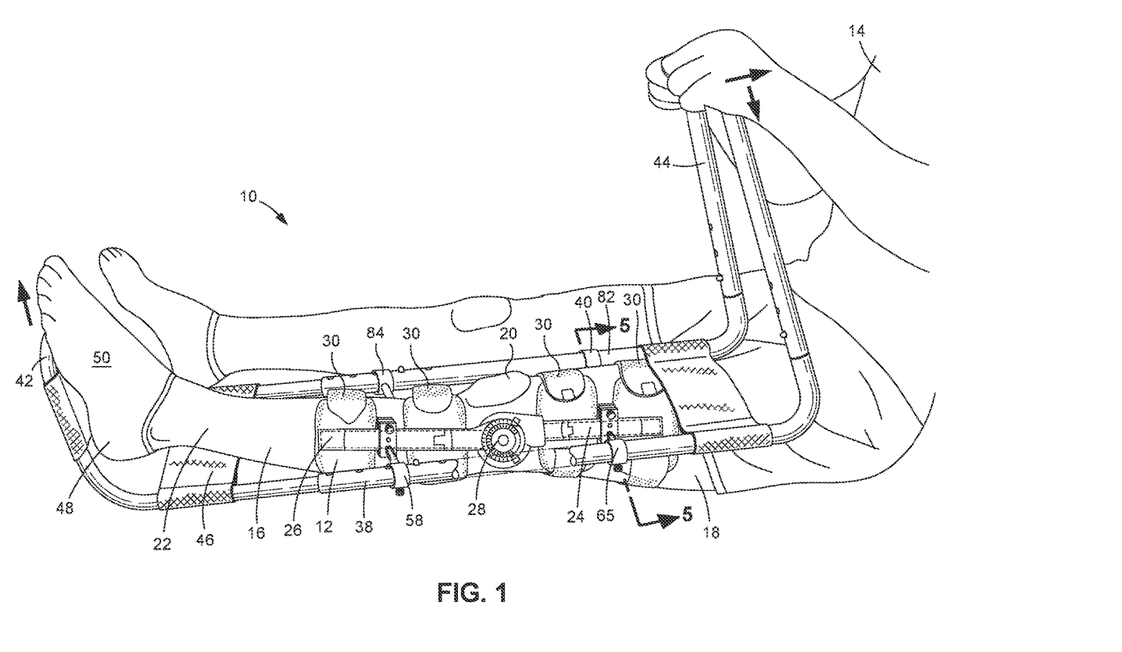
FIG. 1 is a perspective view of a user as wearing a knee brace upon the user's leg and with a knee extension apparatus of an aspect of the present invention as attached to the knee brace.
Figure 2:
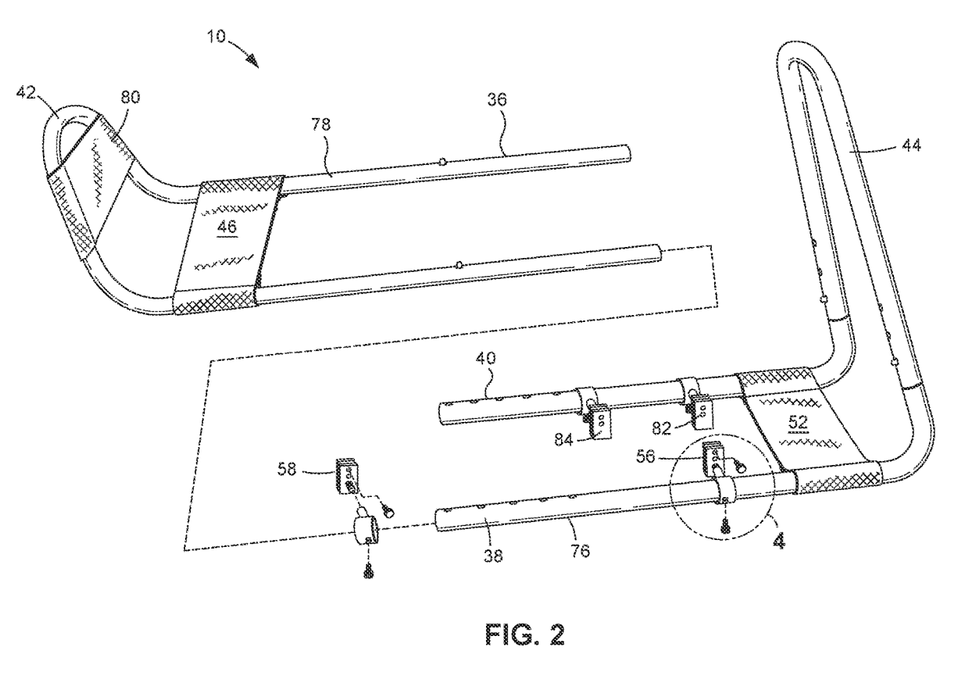
FIG. 2 is an exploded perspective view of the apparatus of FIG. 1.
Figure 3:
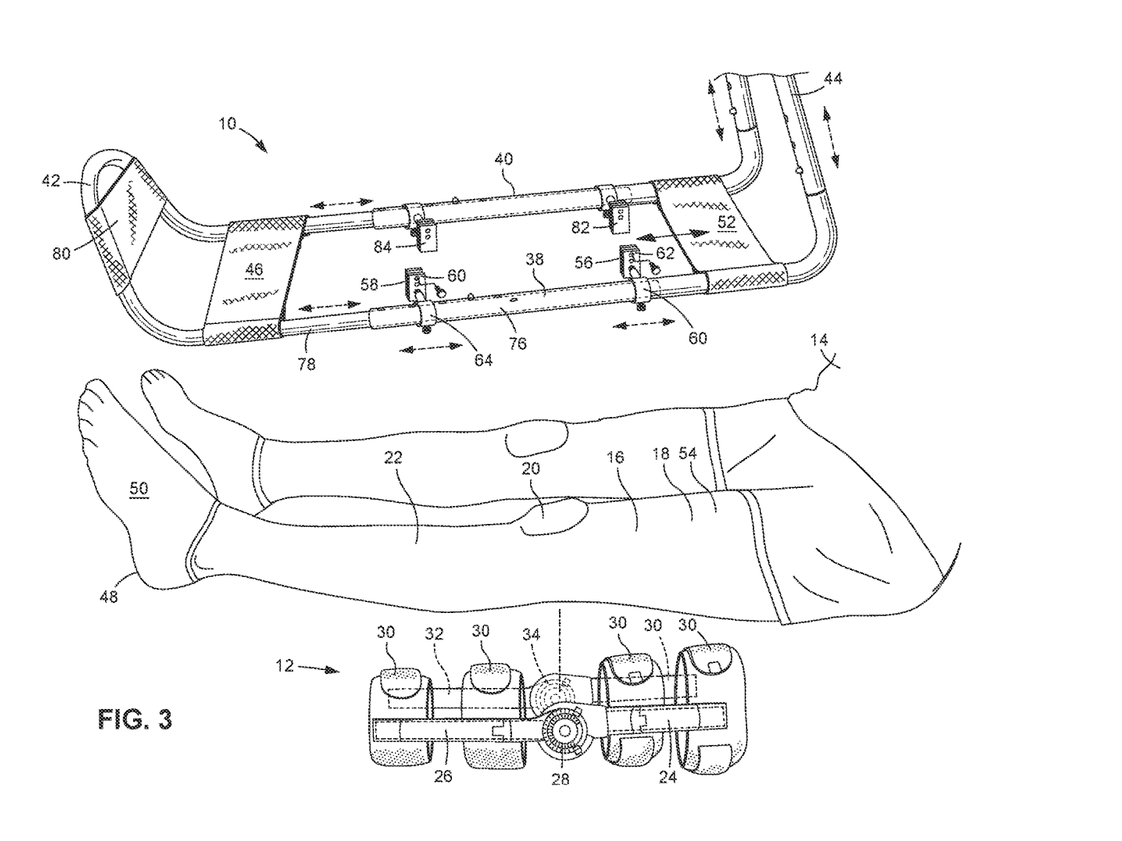
FIG. 3 is an exploded perspective view of the user, the knee brace and the knee extension apparatus.

Referring now to FIGS. 1-3, according to an aspect of the present invention, there is provided a knee extension apparatus 10 for knee extension for use with a knee brace 12 worn about a leg 16 of a user 14. FIG. 1 is a perspective view of the user 14 as wearing the knee brace 12 upon the user's leg 16 and with the knee extension apparatus 10. FIG. 2 is an exploded perspective view of the knee extension apparatus 10 of FIG. 1. FIG. 3 is an exploded perspective view of the user 14, the knee brace 12 and the knee extension apparatus 10.

The knee brace 12 is worn by the user about the leg 16 having an upper leg 18, a knee 20 and a lower leg 22. The knee brace 12 has an upper exterior bar element 24, a lower exterior bar element 26, and an exterior hinge 28 disposed between the upper exterior bar element 24 and the lower exterior bar element 26. The upper exterior bar element 24 is positioned along the upper leg 18 of the user 14 with the knee brace 12 worn by the user 14. The lower exterior bar element 26 is positioned along the lower leg 22 of the user 14 with the knee brace 12 worn by the user 14. The exterior hinge 28 is positioned at the knee 20 of the user 14 with the knee brace 12 worn by the user 14.

In addition, the knee brace 12 may further have an upper interior bar element 30 generally parallel to the upper exterior bar element 24, a lower interior bar element 32 generally parallel to the lower exterior bar element 26, and an interior hinge 34 disposed between the upper interior bar element 30 and the lower interior bar element 32. The upper interior bar element 30 is positioned along the upper leg 18 of the user 14 with the knee brace 12 worn by the user 14. The lower interior bar element 32 is positioned along the lower leg 22 of the user 14 with the knee brace 12 worn by the user 14. The interior hinge 34 is positioned with the knee 20 between the interior hinge 34 and the exterior hinge 28 with the knee brace 12 worn by the user 14.

The knee extension apparatus 10 includes a frame 36 defining a generally elongated rectangular-like frame having a generally parallel first and second frame sides 38, 40, a foot support end 42 and a handle end 44. The foot support end 42 is bent toward the handle end 44. The apparatus 10 further includes a heel support 46. The heel support 46 is disposed adjacent the foot support end 42 and spanning across the first and second frame sides 38, 40. The heel support 46 is sized and configured to engage a heel 48 of the user 14 with a bottom of a foot 50 of the user 14 being disposed against the foot support end 42. The apparatus 10 further includes a thigh support 52 spanning across the first and second frame sides 38, 40. The thigh support 52 is sized and configured to engage a thigh 54 of the user 14 with the foot 50 of the user 14 being disposed against the foot support end 42.

The apparatus 10 further includes an upper exterior attachment member 56 attached to the first frame side 38 and further attachable to the upper exterior bar element 24 of the knee brace 12 with the knee brace 12 being worn by the user 14 and the heel support 46 disposed against the lower leg 22 adjacent the heel 48 of the user 14 and the thigh support 52 disposed against the thigh 54 of the user 14. The apparatus 10 further includes a lower exterior attachment member 58 attached to the first frame side 38 and further attachable to the lower exterior bar element 26 of the knee brace 12 with the knee brace 12 being worn by the user 14 and the heel support 46 disposed against the lower leg 22 adjacent the heel 48 of the user 14 and the thigh support 52 disposed against the thigh 54 of the user 14.

With the above-described configuration the user 14 may utilize the knee extension apparatus 10 while wearing the knee brace 12. The knee brace 12 is of a typical prior art design that includes the upper exterior bar element 24, the lower exterior bar element 26 and the exterior hinge 28. As used herein the upper exterior bar element 24 and the lower exterior bar element 26 are structurally rigid or semi-rigid members that are end-to-end connected by the exterior hinge 28. The exterior hinge 28 facilitate the upper exterior bar element 24 and the lower exterior bar element 26 to be held at the particular angular position with respect to each other. The particular length, thickness, cross-section, material type, and shape of each of the upper exterior bar element 24 and the lower exterior bar element 26 may vary depending upon the particular knee brace 12.

The exterior hinge 38 may include a locking mechanism to as to fix the angular position of the upper exterior bar element 24 and the lower exterior bar element 26 with respect to each other. For example, a locking pin, dial, fastener or other securing arrangement may be implemented as the case may be. The exterior hinge 38 may include indicia as to indicate the desired angulation. Indicia indicating various angles are contemplated to be particularly use for measuring a patient's progress with respect to the amount of knee extension.

It is contemplated that the knee brace 12 is being worn by the user 14 for therapeutic purposes. For example, the user 14 may be a patient recovering from a knee surgery. As is typical, it may be desirable to maintain the upper leg 18 and the lower leg 22 to be held or maintained at a particular angle with respect to each other. This angle may be prescribed or desired to be at a specific angular orientation between the upper leg 18 and the lower leg 22 during different phases of the knee recovery process. Generally speaking, it is often a goal to allow the lower leg 22 to be able to move forwardmost as possible towards an orientation of the lower leg 22 approaching parallel to the upper leg 18 for full knee extension. This facilitates the ligaments, muscles and other structures associated with the knee 20 properly heal and achieve desired mobility.

The knee brace 12 may further have one or more attachment straps 30 of various types that may also include hook and loop type closures. The straps 30 may be a flexible material, such as a fabric that may have a layer of elastomeric rubberized foam. The straps 30 are used to securely (yet removably) affix the knee brace 12 to the leg 16 of the user 14. In particular, the straps 30 are used to secure the knee brace 12 with the upper exterior bar element 24 positioned along the lateral portion of the upper leg 18, the lower exterior bar element 26 positioned along the lateral portion of the lower leg 22, and the exterior hinge 28 positioned along the lateral portion of the knee 20. The straps 30 also provide support radially inward facing support for the knee 20, including the ligaments, muscles and other structures associated with the knee 20. This provides stability in multiple directions and restricts freedom of movement in multiple directions, including rotation of the lower leg 22 relative to the upper leg 18 and lateral buckling of knee 20.

As mentioned above the user 14 may utilize the knee extension apparatus 10 while wearing the knee brace 12. The knee extension apparatus 10 can be used with a knee brace 12 that is not provided by with same entity or manufacturer of the knee extension apparatus 10. Thus, the knee extension apparatus 10 is able to be retro-fitted for use with various different knee braces 12.

The knee extension apparatus 10 allows for the user 14 to exert a force upon the handle end 44 by pulling the handle end 44 down (to extend the knee 20) and toward the torso of the user 14. A force may further be exerted in a direction towards the thigh 54 of the user 14 with the thigh support 52 pressing against the thigh 54 as well. This geometry results in a rotation or pivoting of the knee extension apparatus 10 with the foot support end 42 tending to move the lower leg 22 in an anterior or forward direction with the heel support 46 pressing against the posterior portion of the lower leg 22 adjacent the heel 48. This has the desired effect of encouraging an extension of the knee 20. Importantly, this knee extension may be effected while the user 14 is wearing the knee brace 12. This is contemplated to maintain the upper leg 18, the knee 20 and the lower leg 22 all in proper alignment. In particular, the lower leg 22 is restrained from twisting or longitudinally rotating relative to the knee 20 which may run counter of a desired knee recovery process. As such the knee extension apparatus 10 allows for motion restriction and control of the proper leg alignment while allowing for desired knee extension and leg muscle stretching.

Figure 4:
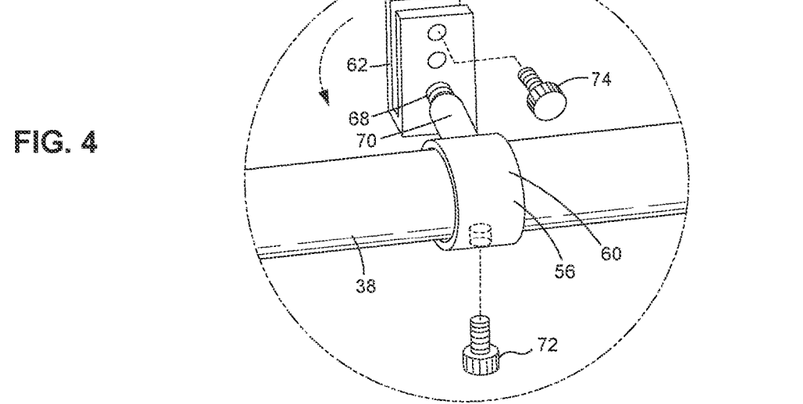
FIG. 4 is an enlarged view of a portion of the apparatus as indicated in the dashed lined circle of FIG. 2.
Figure 5:
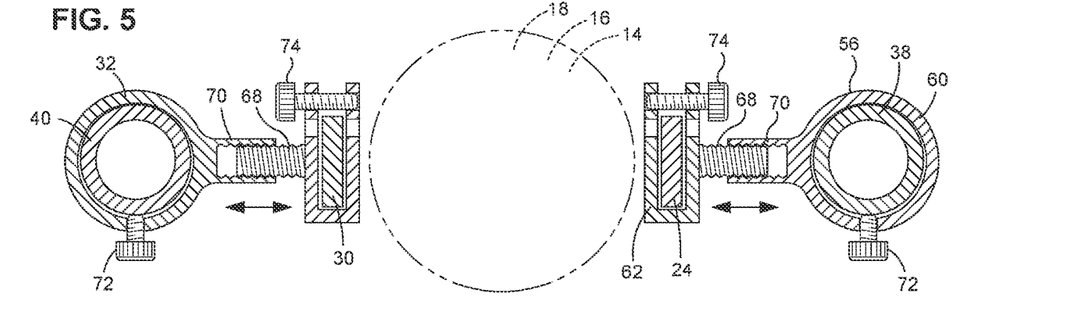
FIG. 5 is a cross-sectional view of a portion of the apparatus and the leg of the user (symbolically indicated in the dashed lined circle) as wearing the knee brace as viewed along axis 5-5 of FIG. 1.

Referring additionally to FIG. 4, there is depicted an enlarged view of a portion of the apparatus 10 as indicated in the dashed lined circle of FIG. 2. In addition, FIG. 5 is a cross-sectional view of a portion of the apparatus 10 and the leg 16 of the user (symbolically indicated in the dashed lined circle) as wearing the knee brace 12 as viewed along axis 5-5 of FIG. 1. The upper exterior bar element 24 and the upper interior bar element 30 of the knee brace 12 are shown in cross section.

According to various embodiments, the upper exterior attachment member 56 may include an upper exterior frame end 60 attached to the first frame side 38 and an upper exterior brace end 62 attachable to the upper exterior bar element 24. The upper exterior frame end 60 may be repositionable along the first frame side 38 in fixed attachment. The ability for the upper exterior frame end 60 to be repositionable along the first frame side 38 is advantageous as this would accommodate differing sizes of the knee brace 12 and different knee braces 12 with differing potential available attachment points along the upper exterior bar element 24.

The upper exterior attachment member 56 may be attachable to the upper exterior bar element 24 of the knee brace 12 with the knee brace 12 being worn by the user 14 and the heel support 46 disposed against the lower leg 22 adjacent the heel 48 of the user 14 and the thigh support 52 disposed against the thigh 54 of the user 14 with a distance between the upper exterior frame end 60 and the upper exterior brace end 62 being adjustable. The ability of the upper exterior attachment member 56 to be adjustable allows for flexibility of the knee extension apparatus 10 to be utilized with a variety of knee braces 12 having differing widths.

The lower exterior attachment member 58 may include a lower exterior frame end 64 attached to the first frame side 38 and a lower exterior brace end 66 attachable to the lower exterior bar element 26. The lower exterior frame end 64 may be repositionable along the first frame side 38 in fixed attachment. The ability for the lower exterior frame end 64 to be repositionable along the first frame side 38 is advantageous as this would accommodate differing sizes of the knee brace 12 and different knee braces 12 with differing potential available attachment points along the lower exterior bar element 26.

The lower exterior attachment member 58 may be attachable to the lower exterior bar element 26 of the knee brace 12 with the knee brace 12 being worn by the user 14 and the heel support 46 disposed against the lower leg 22 adjacent the heel 48 of the user 14 and the thigh support 52 disposed against the thigh 54 of the user 14 with a distance between the lower exterior frame end 64 and the lower exterior brace end 66 being adjustable. The ability of the lower exterior attachment member 58 to be adjustable allows for flexibility of the knee extension apparatus 10 to be utilized with a variety of knee braces 12 having differing widths and lengths.

The apparatus 10 may further include an upper interior attachment member 82 attached to the second frame side 40 and further attachable to the upper interior bar element 30 of the knee brace 12 with the knee brace 12 being worn by the user 14 and the heel support 46 disposed against the lower leg 22 adjacent the heel 48 of the user 14 and the thigh support 52 disposed against the thigh 54 of the user 14. The upper interior attachment member 82 is contemplated to be configured in a similar respect to the upper exterior attachment member 56, but associated with the second frame side 40 and the upper interior bar element 30.

The apparatus may further include a lower interior attachment member 84 attached to the second frame side 40 and further attachable to the lower interior bar element 32 of the knee brace 12 with the knee brace 12 being worn by the user 14 and the heel support 46 disposed against the lower leg 22 adjacent the heel 48 of the user 14 and the thigh support 52 disposed against the thigh 54 of the user 14. The lower interior attachment member 84 is contemplated to be configured in a similar respect to the lower exterior attachment member 58, but associated with the second frame side 40 and the lower interior bar element 32.

The first frame side 38 may be attachable to the upper exterior bar element 24 of the knee brace 12 at a variable angle with the knee brace 12 being worn by the user 14 and the heel support 46 disposed against the lower leg 22 adjacent the heel 48 of the user 14 and the thigh support 52 disposed against the thigh 54 of the user 14. The upper exterior attachment member 56 may be configured to attach the first frame side 38 to the upper exterior bar element 24 at various angles with respective to each other. The knee brace 12 may be configured with the upper exterior bar element 24 disposed at an angle with respect to the lower exterior bar element 26. It this respect the upper exterior bar element 24 and the lower exterior bar element 26 would not be parallel or inline. The user 14 may adjust such angle over time, such as during different phases of an injury or surgery recovery process. When the user 14 is utilizing the knee extension apparatus 10, the knee brace 12 may be worn with the upper exterior bar element 24 disposed at an angle with respect to the lower exterior bar element 26 that may differ from other times when the user 14 is wearing the knee brace 12. The upper exterior attachment member 56 may thus be configured to accommodate for such varying angle of the upper exterior bar element 24 to the lower exterior bar element 26.

The second frame side 40 may be attachable to the upper interior bar element 82 of the knee brace 12 at a variable angle with the knee brace 12 being worn by the user 14 and the heel support 46 disposed against the lower leg 22 adjacent the heel 48 of the user 14 and the thigh support 52 disposed against the thigh 54 of the user 14. Like the upper exterior attachment member 56, the lower exterior attachment member 58 may be configured to attach the first frame side 38 to the lower exterior bar element 26 at various angles with respective to each other.

The apparatus 10 may further include a foot support 80 disposed at the foot support end 42 spanning across the first and second frame sides 38, 40. The foot support 80 is disposed between the heel support 46 and the distal portion of the foot support end 42. During use the apparatus 10 is positioned with the foot support 80 in contact with the bottom of the user's foot 50. The foot support 80 in combination with the heel support 46 is contemplated to generally support the angular orientation of the foot 50 to the lower leg 22 to lock the ankle in position. In addition, the contact between the 50 and the foot support 80 maintains the lateral angular orientation of the foot 50 (i.e., left and right) with respect to the user's ankle and lower leg 22. By maintaining this alignment, this further aids to maintain the connected lower leg 22 which in turn aids to maintain the angular orientation of the lower leg 22 in relation to the user's knee 20.

The frame 36 may be formed of any of those materials which are well known to one of ordinary skill in the art. For example, the material may be of metal, like aluminum, or stiff plastic tubing. The frame 36 may be formed of multiple components. In the embodiment depicted, the frame 36 includes a frame top section 76 and a frame bottom section 78. The overall length of the frame 36 may be adjusted. The frame bottom section 78 may be telescopically received by the frame top section 76 and selectively locked into place, such a via spring pin and hole arrangement. Other portions of the frame 36 may also be adjustable, such as the handle end 44 with yet further telescopically received components that are selectively lockable at differing positions to customize the length or dimensions of the frame 36 as desired. It is contemplated that the frame 36 being separated into components may also facilitate the heel support 46, the thigh support 52 and the foot support 80 to be attached and reattached to the frame 36 as needed.

The heel support, 46, the thigh support 52, and the foot support 80 may be respectively formed of any of those materials which are well known to one of ordinary skill in the art. For example, the material may be an elastic or flexible woven cloth with ends formed into end loops that may be slipped over sections of the frame 36. It is contemplated that the heel support, 46, the thigh support 52, and the foot support 80 may be repositionable along the frame 36 as desired by the user 14. This may be due to differences of the size of the particular user 14. Also, this may be due to allowing for a position along the first and second frame sides 38, 40 so as to avoid putting undue pressure upon certain portion of the leg 16, such as immediately adjacent the knee 20, especially during a surgery recovery process. Further, the particular positioning of the heel support, 46, the thigh support 52, and the foot support 80 may alter the points of leverage or pivot locations of the knee extension apparatus 10 with respect to the leg 16.

Figure 6:
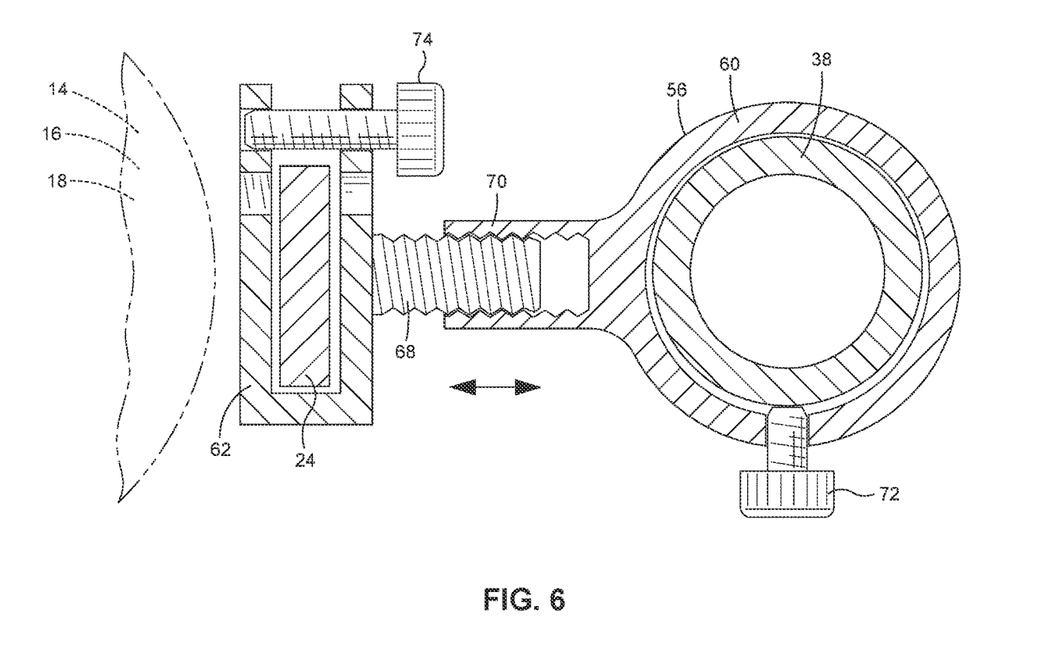
FIG. 6 is an enlarged view of a portion of the apparatus and the leg of the user as wearing the knee brace of FIG. 5.

Referring additionally to FIG. 6, there is depicted an enlarged view of a portion of the apparatus 10 and the leg 16 of the user 14 as wearing the knee brace 12 of FIG. 5. In particular, an embodiment of the upper exterior attachment member 56 is described. In the embodiment depicted, the upper exterior brace end 62 may have a u-shaped or clamshell-shaped cross-section that is configured to receive the upper exterior bar element 24. The upper exterior brace end 62 may include a threaded base 68 extending there from. The upper exterior attachment member 56 includes the upper exterior frame end 60 in the form of a collar that is configured to receive the first frame side 38 there through. An internally threaded shank 70 may extend from the upper exterior frame end 60. The shank 70 is sized and configured to threadedly receive the corresponding threaded base 68 therein. With this general configuration the upper exterior attachment member 56 is used to attach the first frame side 38 to the upper exterior bar element 24.

A screw 72 is provided to threadedly engage the upper exterior frame end 60. The screw 72 may extend through the upper exterior frame end 60 to distally engage the first frame side 38. It is understood that the screw 72 may be readily used to attach the upper exterior frame end 60 of the upper exterior attachment member 56 to the first frame side 38. The screw 72 may be loosened to disengage the upper exterior frame end 60 from the first frame side 38 or to reposition and attach the upper exterior frame end 60 along the first frame side 38. Where the cross-sectional shape of the first frame side 38 is circular, such as in the embodiment depicted, the collar-like shape of the upper exterior frame end 60 may be selectively attached to the first frame side 38 with respect to an angular orientation about a longitudinal axis of the first frame side 38.

The threaded base 68 may be screwed into the shank 70 to connect the upper exterior frame end 60 with the upper exterior brace end 62. This arrangement also allows the upper exterior frame end 60 to be variably spaced from the upper exterior brace end 62. In this respect as mentioned above, the distance between the upper exterior frame end 60 and the upper exterior brace end 62 may be adjustable.

In addition, the threaded base 68 and shank 70 arrangement allows for a selective angular orientation of the upper exterior frame end 60 about a longitudinal axis of the threaded base 68 with respect to the exterior brace end 62. This allows for the first frame side 38 to be attachable to the upper exterior bar element 24 of the knee brace 12 at a variable angle with the knee brace 12 being worn by the user 14 and the heel support 46 disposed against the lower leg 22 adjacent the heel 48 of the user 14 and the thigh support 52 disposed against the thigh 54 of the user 14. This variable angle adjustability is contemplated to facilitate attachment of the first frame side 38 to the knee brace 12 as it is contemplated that the knee brace 12 may be adjusted to have the upper exterior bar element 24 at various angles with respective to the lower exterior bar element 26. With the knee brace 12 bent (i.e., the upper exterior bar element 24 and the lower exterior bar element 26 being not parallel), the first frame side 38 would not necessarily be parallel of either the upper exterior bar element 24 or the lower exterior bar element 26.

As mentioned above, the upper exterior brace end 62 may have a u-shaped or clamshell-shaped cross-section that is configured to receive the upper exterior bar element 24. In this respect the knee brace 12 is contemplated to heave the upper exterior bar element 24 having a generally rectangular cross-section. The upper exterior brace end 62 may have a slot to receive such rectangular cross-section. A screw 74 may be provided that threadedly engages the upper exterior brace end 62 to tighten the upper exterior brace end 62 against the upper exterior bar element 24 for secure engagement of the upper exterior brace end 62 with the upper exterior bar element 24. Different threaded engagement holes may be provided in the upper exterior brace end 62 to accommodate different sizes of the upper exterior bar element 24. The screw 74 may be loosened to disengage the upper exterior brace end 62 from the upper exterior bar element 24 or to reposition and attach the upper exterior brace end 62 along the upper exterior bar element 24.

It is contemplated that the lower exterior attachment member 58, the upper interior attachment member 82 and the lower interior attachment member 84 may each be constructed similarly to the upper exterior attachment member 56.

Figure 7:
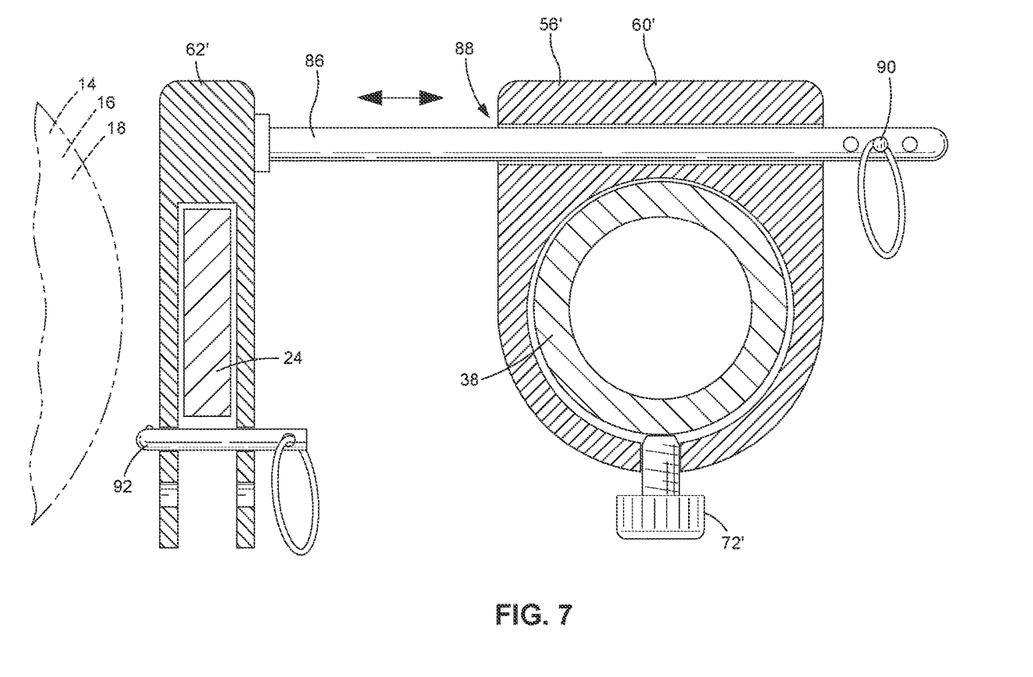
FIG. 7 is an enlarged view similar to that of FIG. 6, however, with a portion of the apparatus according to another embodiment and the leg of the user as wearing the knee brace.

Referring now to FIG. 7, there is depicted an enlarged view similar to that of FIG. 6, however, with a portion of the apparatus 10 according to another embodiment and the leg 16 of the user as wearing the knee brace 12. In this embodiment, there is provided upper exterior attachment member 56' as an alternative to the upper exterior attachment member 56. The upper exterior attachment member 56' includes an upper exterior frame end 60' and an upper exterior brace end 62'. The upper exterior frame end 60' may take the form of a collar that is configured to receive the first frame side 38 there through. A screw 72' is provided to threadedly engage the upper exterior frame end 60'. The screw 72 may extend through the upper exterior frame end 60' to distally engage the first frame side 38. It is understood that the screw 72' may be readily used to attach the upper exterior frame end 60' of the upper exterior attachment member 5'6 to the first frame side 38. The screw 72' may be loosened to disengage the upper exterior frame end 60' from the first frame side 38 or to reposition and attach the upper exterior frame end 60' along the first frame side 38. Where the cross-sectional shape of the first frame side 38 is circular, such as in the embodiment depicted, the collar-like shape of the upper exterior frame end 60' may be selectively attached to the first frame side 38 with respect to an angular orientation about a longitudinal axis of the first frame side 38.

The upper exterior attachment member 56' may further include a shaft 86 that extends from the upper exterior brace end 62'. The upper exterior frame end 60' may include a through hole 88 formed there through. The through hole 88 is sized and configured to receive the shaft 86 there through. The upper exterior frame end 60' may slide toward and away from the upper exterior brace end 62'. This arrangement also allows the upper exterior frame end 60' to be variably spaced from the upper exterior brace end 62'. In this respect the distance between the upper exterior frame end 60' and the upper exterior brace end 62' may be adjustable. The shaft 86 may include one or more holes that are sized and configured to receive a pin 90 there through to capture or otherwise maintain and prevent the upper exterior frame end 60' from disengaging from the shaft 86. In addition, the shaft 86 through the upper exterior frame end 60' arrangement allows for accommodating differing angular orientations of the first frame side 38 to the attached the upper exterior bar element 24.

The upper exterior brace end 62' may have a u-shaped or clamshell-shaped cross-section that is configured to receive the upper exterior bar element 24. In this respect the knee brace 12 is contemplated to have the upper exterior bar element 24 having a generally rectangular cross-section. The upper exterior brace end 62' may have a slot to receive such rectangular cross-section. A pin 92 may be provided that threadedly engages the upper exterior brace end 62' to retain the upper exterior bar element 24 for secure engagement of the upper exterior brace end 62' with the upper exterior bar element 24. Different positioned engagement holes may be provided in the upper exterior brace end 62' to accommodate different sizes of the upper exterior bar element 24.

According to another aspect of the invention, there is provided a method for knee extension for use with the knee brace 12 worn about the leg 16 of the user 14. The method includes wearing the knee brace 12 by the user 14 with the upper exterior bar element 24 being positioned along the upper leg 18 of the user 14, with the lower exterior bar element 26 being positioned along the lower leg 22 of the user 14, and with the exterior hinge 28 being positioned at the knee 20 of the user 14. The method further includes providing the knee extension apparatus 10. The heel support 46 is disposed adjacent the foot support end 42 and spanning across the first and second frame sides 38, 40. The method further includes positioning the apparatus 10 on the user 14 with the leg 16 of the user 14 extending generally along and between the first and second frame sides 38, 40 with the heel 48 of the leg 16 of the user 14 supported by the heal support 46 and the thigh support 52 disposed against the thigh 54 of the user 14. The method further includes attaching the first frame side 38 to the upper exterior bar element 24. The method further includes attaching the first frame side 38 to the lower exterior bar element 26. The method further includes pulling the handle end 44 towards a torso of the user 14.

According to various embodiments, the step of attaching the first frame side 38 to the upper exterior bar element 24 may include providing an upper exterior attachment member 56 attached to the first frame side 38 and the upper exterior bar element 24. The step of attaching the first frame side 38 to the upper exterior bar element 24 may further include repositioning the upper exterior attachment member 56 along the first frame side 38 in fixed attachment. The step of attaching the first frame side 38 to the upper exterior bar element 24 may further include adjusting a length of the upper exterior attachment member 56. The step of attaching the first frame side 38 to the lower exterior bar element 26 may include providing a lower exterior attachment member 58 attached to the first frame side 38 and the lower exterior bar element 26. The step of attaching the first frame side 38 to the lower exterior bar element 26 may further include repositioning the lower exterior attachment member 26 along the first frame side 38 in fixed attachment. The step of attaching the first frame side 38 to the lower exterior bar element 26 may further include adjusting a length of the lower exterior attachment member 58.

Further, the knee brace 12 may further have the upper interior bar element 30 generally parallel to the upper exterior bar element 24, the lower interior bar element 32 generally parallel to the lower exterior bar element 26, and the interior hinge 34 disposed between the upper interior bar element 30 and the lower interior bar element 32. The upper interior bar element 30 may be positioned along the upper leg 18 of the user 14 with the upper leg 18 between the upper exterior bar element 24 and the upper interior bar element 30 with the knee brace 12 worn by the user 14. The lower interior bar element 32 may positioned along the lower leg 22 of the user 14 with the lower leg 22 between the lower exterior bar element 26 and the lower interior bar element 32 with the knee brace 12 worn by the user 14. The interior hinge 34 may positioned with the knee 20 between the exterior hinge 28 and the interior hinge 34 with the knee brace 12 worn by the user 14. The step of wearing the knee brace 12 may further include wearing the knee brace 12 by the user 14 with the upper leg 18 between upper interior bar element 30 and the upper exterior bar element 24, the lower leg 22 between the lower exterior bar element 26 and the lower interior bar element 32, and the knee between the exterior hinge 28 and the interior hinge 34. The method may further include attaching the second frame side 40 to the upper interior bar element 30 and attaching the second frame side 40 to the lower interior bar element 32.

According to another aspect of the invention, there is provided an integrated knee extension system for knee extension. The system includes the knee brace 12 and the knee extension apparatus 10 as contemplated above.

The particulars shown herein are by way of example only for purposes of illustrative discussion, and are presented in the cause of providing what is believed to be the most useful and readily understood description of the principles and conceptual aspects of the various embodiments set forth in the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A knee extension apparatus for knee extension for use with a knee brace worn about a leg of a user, the knee brace having an upper exterior bar element, a lower exterior bar element, and an exterior hinge disposed between the upper exterior bar element and the lower exterior bar element, the upper exterior bar element being positioned along an upper leg of the user with the knee brace worn by the user, the lower exterior bar element being positioned along a lower leg of the user with the knee brace worn by the user, the exterior hinge being positioned at the knee of the user with the knee brace worn by the user, the knee extension apparatus comprising:
   a frame defining a generally elongated rectangular-like frame having a generally parallel first and second frame sides, a foot support end and a handle end, the foot support end being bent toward the handle end;
   a heel support, the heel support being disposed adjacent the foot support end and spanning across the first and second frame sides, the heel support being sized and configured to engage a heel of the user with a bottom of a foot of the user being disposed against the foot support end;
   a thigh support spanning across the first and second frame sides, the thigh support being sized and configured to engage a thigh of the user with the foot of the user being disposed against the foot support end;
   an upper exterior attachment member attached to the first frame side and further attachable to the upper exterior bar element of the knee brace with the knee brace being worn by the user and the heel support disposed against the lower leg adjacent the heel of the user and the thigh support disposed against the thigh of the user; and
   a lower exterior attachment member attached to the first frame side and further attachable to the lower exterior bar element of the knee brace with the knee brace being worn by the user and the heel support disposed against the lower leg adjacent the heel of the user and the thigh support disposed against the thigh of the user.

2. The knee extension apparatus of claim 1 wherein the upper exterior attachment member includes an upper exterior frame end attached to the first frame side and an upper exterior brace end attachable to the upper exterior bar element.

3. The knee extension apparatus of claim 1 wherein the upper exterior attachment member is attachable to the upper exterior bar element of the knee brace with the knee brace being worn by the user and the heel support disposed against the lower leg adjacent the heel of the user and the thigh support disposed against the thigh of the user with a distance between the upper exterior frame end and the upper exterior brace end being adjustable.

4. The knee extension apparatus of claim 1 wherein the lower exterior attachment member includes a lower exterior frame end attached to the first frame side and a lower exterior brace end attachable to the lower exterior bar element.

5. The knee extension apparatus of claim 4 wherein the lower exterior attachment member is attachable to the lower exterior bar element of the knee brace with the knee brace being worn by the user and the heel support disposed against the lower leg adjacent the heel of the user and the thigh support disposed against the thigh of the user with a distance between the lower exterior frame end and the lower exterior brace end being adjustable.

6. The knee extension apparatus of claim 1 wherein the upper exterior attachment member includes an upper exterior frame end and an upper exterior brace end, the upper exterior frame end is attached to the first frame side and the upper exterior brace end is attachable to the upper exterior bar element of the knee brace with the knee brace being worn by the user and the heel support disposed against the lower leg adjacent the heel of the user and the thigh support disposed against the thigh of the user.

7. The knee extension apparatus of claim 6 wherein the upper exterior frame end is repositionable along the first frame side in fixed attachment.

8. The knee extension apparatus of claim 7 wherein the lower exterior frame end is repositionable along the first frame side in fixed attachment.

9. The knee extension apparatus of claim 1 wherein the knee brace further has an upper interior bar element generally parallel to the upper exterior bar element, a lower interior bar element generally parallel to the lower exterior bar element, and an interior hinge disposed between the upper interior bar element and the lower interior bar element, the lower interior bar element is positioned along a lower leg of the user with the knee brace worn by the user, the interior hinge is positioned with the knee between the interior hinge and the exterior hinge with the knee brace worn by the user, the apparatus further includes:
   an upper interior attachment member attached to the second frame side and further attachable to the upper interior bar element of the knee brace with the knee brace being worn by the user and the heel support disposed against the lower leg adjacent the heel of the user and the thigh support disposed against the thigh of the user.

10. The knee extension apparatus of claim 9 further includes:
   a lower interior attachment member attached to the second frame side and further attachable to the lower interior bar element of the knee brace with the knee brace being worn by the user and the heel support disposed against the lower leg adjacent the heel of the user and the thigh support disposed against the thigh of the user.

11. The knee extension apparatus of claim 1 wherein the first frame side is attachable to the upper exterior bar element of the knee brace at a variable angle with the knee brace being worn by the user and the heel support disposed against the lower leg adjacent the heel of the user and the thigh support disposed against the thigh of the user.

12. A method for knee extension for use with a knee brace worn about a leg of a user, the knee brace having an upper exterior bar element, a lower exterior bar element, and an exterior hinge disposed between the upper exterior bar element and the lower exterior bar element, the method comprising:
(a) wearing the knee brace by the user with the upper exterior bar element being positioned along an upper leg of the user, with the lower exterior bar element being positioned along a lower leg of the user, and with the exterior hinge being positioned at the knee of the user;
(b) providing a knee extension apparatus including:
a frame defining a generally elongated rectangular-like frame having a generally parallel first and second frame sides, a foot support end and a handle end, the foot support end being bent toward the handle end;
a heel support, the heel support being disposed adjacent the foot support end and spanning across the first and second frame sides, the heel support being sized and configured to engage a heel of the user with a bottom of a foot of the user being disposed against the foot support end; and
a thigh support spanning across the first and second frame sides, the thigh support being sized and configured to engage a thigh of the user with the foot of the user being disposed against the foot support end;
(c) positioning the knee extension apparatus on the user with the leg of the user extending generally along and between the first and second frame sides with a heel of the leg of the user supported by the heal support and the thigh support disposed against the thigh of the user;
(d) attaching the first frame side to the upper exterior bar element; the first frame side to the upper exterior bar element includes providing an upper exterior attachment member attached to the first frame side and the upper exterior bar element;
(e) attaching the first frame side to the lower exterior bar element; the first frame side to the lower exterior bar element includes providing a lower exterior attachment member attached to the first frame side and the lower exterior bar element and
(f) pulling the handle end towards a torso of the user.

13. The method of claim 12 wherein step (d) of attaching the first frame side to the upper exterior bar element further includes repositioning the upper exterior attachment member along the first frame side in fixed attachment.

14. The method of claim 12 wherein step (d) of attaching the first frame side to the upper exterior bar element further includes adjusting a length of the upper exterior attachment member.

15. The method of claim 12 wherein step (d) of attaching the first frame side to the lower exterior bar element further includes repositioning the lower exterior attachment member along the first frame side in fixed attachment.

16. The method of claim 12 wherein step (d) of attaching the first frame side to the lower exterior bar element further includes adjusting a length of the lower exterior attachment member.

17. The method of claim 12 wherein the knee brace further has an upper interior bar element generally parallel to the upper exterior bar element, a lower interior bar element generally parallel to the lower exterior bar element, and an interior hinge disposed between the upper interior bar element and the lower interior bar element, the upper interior bar element is positioned along the upper leg of the user with the upper leg between the upper exterior bar element and the upper interior bar element with the knee brace worn by the user, the lower interior bar element is positioned along the lower leg of the user with the lower leg between the lower exterior bar element and the lower interior bar element with the knee brace worn by the user, the interior hinge is positioned with the knee between the exterior hinge and the interior hinge with the knee brace worn by the user, wherein step (a) of wearing the knee brace further includes wearing the knee brace by the user with the upper leg between upper interior bar element and the upper exterior bar element, the lower leg between the lower exterior bar element and the lower interior bar element, and the knee between the exterior hinge and the interior hinge.

18. The method of claim 17 further includes attaching the second frame side to the upper interior bar element and attaching the second frame side to the lower interior bar element.

19. An integrated knee extension system for knee extension, the integrated knee extension system comprising:
a knee brace worn about a leg of a user, the knee brace having an upper exterior bar element, a lower exterior bar element, and an exterior hinge disposed between the upper exterior bar element and the lower exterior bar element, the upper exterior bar element being positioned along an upper leg of the user with the knee brace worn by the user, the lower exterior bar element being positioned along a lower leg of the user with the knee brace worn by the user, the exterior hinge being positioned at the knee of the user with the knee brace worn by the user; and
a knee extension apparatus:
a frame defining a generally elongated rectangular-like frame having a generally parallel first and second frame sides, a foot support end and a handle end, the foot support end being bent toward the handle end;
a heel support, the heel support being disposed adjacent the foot support end and spanning across the first and second frame sides, the heel support being sized and configured to engage a heel of the user with a bottom of a foot of the user being disposed against the foot support end;
a thigh support spanning across the first and second frame sides, the thigh support being sized and configured to engage a thigh of the user with the foot of the user being disposed against the foot support end;
an upper exterior attachment member attached to the first frame side and further attachable to the upper exterior bar element of the knee brace with the knee brace being worn by the user and the heel support disposed against the lower leg adjacent the heel of the user and the thigh support disposed against the thigh of the user; and
a lower exterior attachment member attached to the first frame side and further attachable to the lower exterior bar element of the knee brace with the knee brace being worn by the user and the heel support disposed against the lower leg adjacent the heel of the user and the thigh support disposed against the thigh of the user.

* * * * *